United States Patent
Johnson et al.

(10) Patent No.: US 7,314,626 B2
(45) Date of Patent: *Jan. 1, 2008

(54) USE OF PEPTIDE VECTORS TO IMPROVE THE IMMUNE RESPONSE TO ANTIGENS

(75) Inventors: Mark Elliott Johnson, Bellevue, WA (US); Fiona Hamilton Day, Shoreline, WA (US); Michel Kaczorek, Montferrier sur Lez (FR); Jamal Temsamani, Nimes (FR)

(73) Assignee: SYNT:EM S.A., Nimes (FR)

( * ) Notice: Subject to any disclaimer, the term of this patent is extended or adjusted under 35 U.S.C. 154(b) by 474 days.

This patent is subject to a terminal disclaimer.

(21) Appl. No.: 10/270,010

(22) Filed: Oct. 15, 2002

(65) Prior Publication Data

US 2004/0072340 A1    Apr. 15, 2004

(30) Foreign Application Priority Data

Oct. 16, 2001    (EP) .................... 01402671

(51) Int. Cl.
| | | |
|---|---|---|
| *A61K 39/00* | (2006.01) | |
| *A61K 39/12* | (2006.01) | |
| *A61K 39/145* | (2006.01) | |
| *A61K 39/385* | (2006.01) | |
| *A61K 47/00* | (2006.01) | |
| *A61K 38/00* | (2006.01) | |
| *C12P 21/00* | (2006.01) | |
| *C12N 15/09* | (2006.01) | |

(52) U.S. Cl. .................. 424/193.1; 424/184.1; 424/192.1; 424/204.1; 424/206.1; 424/278.1; 435/69.1; 435/69.4; 435/69.7; 514/2

(58) Field of Classification Search ............ 424/184.1, 424/186.1, 192.1, 193.1, 196.11, 204.1; 530/300, 530/317, 324, 325, 326, 327, 350; 514/2, 514/9, 12, 13, 14, 15, 16, 17, 18, 19
See application file for complete search history.

(56) References Cited

U.S. PATENT DOCUMENTS

| | | | | | |
|---|---|---|---|---|---|
| 4,474,757 | A | * | 10/1984 | Arnon et al. | ............ 424/186.1 |
| 5,807,746 | A | * | 9/1998 | Lin et al. | .................... 435/375 |
| 5,846,743 | A | * | 12/1998 | Janmey et al. | ............... 435/7.8 |
| 6,881,825 | B1 | * | 4/2005 | Robbins et al. | ............. 530/327 |

FOREIGN PATENT DOCUMENTS

| | | | |
|---|---|---|---|
| FR | 2767323 | | 8/1998 |
| FR | 2786398 | | 11/1999 |
| WO | WO 99/07728 | * | 2/1999 |
| WO | WO 01/15511 | * | 3/2001 |
| WO | WO 0202595 | | 1/2002 |

OTHER PUBLICATIONS

Nakamura et al., Journal of Biological Chemistry, vol. 263 No. 32, pp. 16709-16713 (Nov. 1988).*
Kawano et al., Journal of Biological Chemistry, vol. 265 No. 26, pp. 15365-15367 (Sep. 1990).*
Rao, Archives of Biochemistry and Biophysics, vol. 361 No. 1, pp. 127-134 (Jan. 1999).*
Matsuzaki et al., Biochemistry, vol. 36 No. 32, pp. 9799-9806 (Aug. 1997).*
Bowie et al., Science, Colume 247 No. 4948, pp. 1306-1310 (Mar. 1990).*
Derossi D et al, "Trojan peptides: the penetratin system for intracellular delivery", Trends in Cell Biology, Elsevier Science Ltd, vol. 8, Feb. 1998, pp. 84-87.

* cited by examiner

*Primary Examiner*—Zachariah Lucas
(74) *Attorney, Agent, or Firm*—Bell, Boyd & Lloyd LLP

(57) ABSTRACT

The invention relates to conjugates of an antigen coupled to a linear derivative of a β-stranded antibiotic peptide, which are useful for immunogenic agents to enhance a CTL response. Two groups of preferred peptides are derived from the antibiotics protegrin and tachyplesin.

7 Claims, 4 Drawing Sheets

USE OF PEPTIDE VECTORS TO IMPROVE THE IMMUNE RESPONSE TO ANTIGENS

FIELD OF INVENTION

The present invention relates generally to the field of immunology and vaccine technology. More specifically, the present invention relates to methods of delivering antigens into cells in order to enhance their immune response for use in vaccination and prophylaxis.

BACKGROUND OF THE INVENTION

The host immune system provides a sophisticated defence mechanism that enables the recognition and elimination of foreign entities, such as infections agents or neoplasms, from the body. When functioning properly, an effective immune system distinguishes between foreign invaders and the host's own tissues. The first response to foreign agents is the secretion of antibodies that are able to recognize, block and destroy microbial agents. However, this response is often not sufficient because in some cases, such as viral particles, the pathogens are able to escape B cell antibody response by rapidly entering into target cells where the antibodies cannot reach them. The pathogen can then replicate intracellularly and infect other peripheral cells. The challenge for scientists is to enhance the T-cell response against microbial agents. T-cell response is the capacity of the immune system to raise a special type of lymphocytes [CD4+, CD8+] that are able to recognize specifically the infected cells and destroy them. This mechanism of T-cell response is complementary to the B-cell antibody response and both are needed to elicit an efficient immune response. As an example, an efficient vaccine against HIV infection is a long process because of the difficulty to generate a CTL response against various vaccine candidates.

Dendritic cells (DCs) are efficient antigen presenting cells (APC) that initiate immune response to peptide antigens associated with class I and II MHC (Freudenthal, P. S. and Steinman, R. M., Proc. Natl. Acad. Sci. USA 87:7698, 1990; Steinman, R. M., Ann. Rev. Immune. 9:271, 1991). DCs represent a small subpopulation of widely distributed, bone marrow-derived leucocytes, which are the only natural antigen presenting cells able to prime naive T cells. They activate both CD4+ and CD8+ T lymphocyte primary immune response, and are at least as effective as other APCs such as monocytes in stimulating secondary immune responses (Peters et al., Immunol. Today L7:273, 1997).

In order to stimulate T lymphocyte responses, peptide fragments from antigens contained in a vaccine must first be bound to peptide binding receptors (major histocompatibility complex [MHC] class I and II molecules) that display the antigenic peptides on the surface of antigen presenting cells (APCs). T lymphocytes produce an antigen receptor that they use to monitor the surface of APCs for the presence of foreign peptides. Current models of antigen processing and presentation to T lymphocytes suggest that two principle pathways exist. In brief, exogenous antigens are internalised into the endocytic compartments of APCs where they are hydrolysed into peptides, some of which become bound to MHC class II molecules. The mature MHC class II/peptide complexes are then transported to the cell surface for presentation to class II-restricted $CD4^+$ T lymphocytes. In contrast, for the MHC class I molecules, endogenous antigens are degraded in the cytoplasm by the action of a proteolytically active particle known as the proteasome before their transport into the endoplasmic reticulum, where they bind to nascent MHC class I molecules. Stable class I/peptide complexes are transported through Golgi apparatus to the cell surface to $CD8^+$ CTL. Because the CTL response is crucial for protection against many viral or parasitic infections and some tumour cells, several new vaccine strategies have been proposed: 1) Immunostimulating complexes (Takahasci et al. 1990. Nature 344:873); 2) antigen-loaded pH-sensitive liposomes (Nair et al. 1992. J. Exp. Med. 175:609); 3) recombinant bacteria expressing foreign antigens (Tuner et al. 1993, Infect. Immun. 61:5374; Ikonomidis et al. 1994. J. Exp. Med 180:2209); 4) bacterial toxins fused to CTL epitopes (Donnelly et al. 1993. Proc; Natl. Acad. Sci USA 90:3530); 5) particulate antigens (Schirmbeck et al. 1994. Eur. J. Immunol 24:2068, Layton et al, 1993. J. Immunol 151:1097); 6) use of various vectors (Schutze-Redelmeier et al. 1996, J. Immunology 157:650-655; Schluesener 1996, J Neurosci Res 46:258-262); and 7) naked DNA injected in muscle cells (Ulmer et al. 1993. Science 259:1745). This variety of strategies reflects the inherent difficulty of delivering antigens intracellularly in order to elicit a CTL response. In many cases, these approaches have a poor in vivo efficiency and are limited by safety considerations, immune responses against the vector, and cost.

In addition to the immune system, mammals are known to produce small peptides which have direct antimicrobial activity. Most of these peptides act by causing direct lysis of the membrane of prokaryotes. A major family of these peptides are β-stranded antibiotic peptides linked by disulphide bonds. Members of the family include defensins (Lehrer et al, 1991, Cell 64:229-230; Lehrer et al, 1993, Ann. Rev. Immunol. 11:105-128), protegrins (Kokryakov et al, 1993, FEBS 337:231-236) and tachyplesins (Nakamura et al, 1988, J. Biol. Chem. 236:16709-16713; Miyata et al, 1989, J. Biochem. 106:663-668).

Peptides of these classes are known to be able to pass through the membranes of mammalian cells, though due to the differences between bacterial and mammalian cell membranes, the peptides are non-toxic to mammalian cells.

WO99/07728 describes a number of derivatives of these peptides as vectors for the introduction of substances to cells or for substances to pass through the blood-brain barrier. These derivatives include linear derivatives in which the peptides do not have disulphide bonds. The absence of disulphide bonds is brought about by substitution of cysteine residues, or blocking their terminal thiol groups.

DISCLOSURE OF THE INVENTION

The applicants have surprisingly found that when peptide vectors based upon the peptides of WO99/07728 are used to attach an antigen, the resulting product can be taken up by antigen presenting cells which are then able to process the antigen and display the antigen on its surface in a manner to facilitate a CTL response. It has been found that the CTL response is enhanced in comparison to the use of the antigen alone.

In a first aspect, the invention provides a conjugate of an antigen coupled to a linear derivative of a β-stranded antibiotic peptide. Preferably, these linear derivatives do not exhibit antibacterial activity.

The invention also provides a pharmaceutical composition comprising said conjugate in a pharmaceutically acceptable carrier.

In another aspect, the invention provides a method of enhancing an immune response to an antigen in a mammal, said method comprising administering to the mammal an effective amount of a conjugate of said antigen coupled to a linear derivative of a β-stranded antibiotic peptide.

The invention also provides the use of a conjugate of an antigen coupled to a linear derivative of a β-stranded antibiotic peptide for the manufacture of a medicament for enhancing an immune response to said antigen in a mammal.

The invention also provides a conjugate of an antigen coupled to a linear derivative of a β-stranded antibiotic peptide for use in a method of enhancing an immune response to said antigen in a mammal.

DETAILED DESCRIPTION OF THE INVENTION

Figure 1:
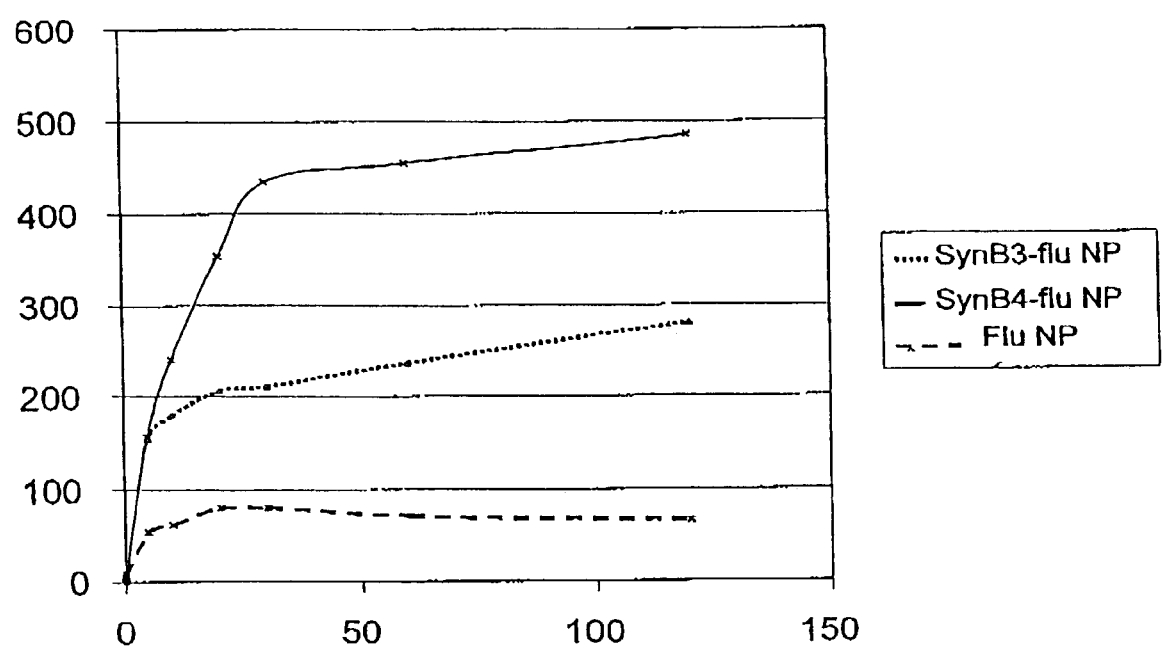
FIG. 1 shows the uptake of conjugates SynB3-fluNP and SynB4-fluNP by K562 cells, together with a control fluNP peptide. The x axis is time in minutes and the y axis denotes Mean Fluorescence Intensity.

Linear Derivative of a β-Stranded Antibiotic Peptide.

This term refers to any mammalian β-stranded antibiotic peptide which has been modified to remove internal disulphide bonds formed between cysteine residues, and optionally further modified by substitution, insertion or deletion in a manner which retains the ability of the peptide to cross the membrane of a mammalian cell.

Modification to remove disulphide bonds may be achieved by chemically blocking the thiol group (e.g. by conversion to an R-thio group such as methyl-thio), or by substitution of the cysteine residue by another amino acid, such as serine, alanine or glycine.

Since a disulphide bond requires two cysteine residues, it is of course possible to leave one unmodified residue in the peptide though is this not preferred, so as to avoid dimers forming.

In one aspect, the linear peptide may be defined as a peptide of structure: Nter-Mid-Cter, in which Mid is a peptide of formula (I):

X1/3-(X1/2 or a bond)-(X or a bond)-X3-(X1 or a bond)-X1-X1/2-(X2/3 or a bond)-Db-(X2/3 or a bond)-X1/3    (SEQ ID NO:1);

where Db is either X3-X3 or X1-X1; and wherein Nter is either an N-terminus or

X1/X3-X1-X1/2-X1-X3    (SEQ ID NO:2); and wherein Cter is either a C-terminus or

X1/2-X1/2-X2/3-X1/2-X1-X3    (SEQ ID NO:3).

in which:
 each X1, which may be identical or different, represents an amino acid residue for which the side chain is non-polar;
 each X2, which may be identical or different, represents an amino acid residue for which the side chain is polar; and
 each X3, which may be identical or different, represents an amino acid residue for which the side chain is basic;
 X is any one of X1, X2 and X3;

wherein said peptide is linear (i.e. does not contain any intra-molecular disulphide bonds) and retains the ability to cross a mammalian membrane;

or a fragment thereof retaining the ability to cross a mammalian membrane.

In the above peptide, it is preferred that if the value indicated as "X1 or a bond" is a bond, then there is a residue X2 or X3 at the position indicated as the first (from the N- to C terminal direction) occurrence of "X2/3 or a bond". Likewise, where the latter is a bond, it is preferred that the former is X1.

Amino acids which have non-polar side chains include alanine, glycine, valine, leucine, isoleucine, proline, phenylalanine, methionine, tryptophan, cysteine, norleucine, cysteine$^{ACm}$, penicillamine, proline, norvaline, phenylglycine, Abu, carboxylic amino-1-cyclohexane acid, Aib, carboxylic 2-aminotetraline, 4-bromophenylalanine, tert-Leucine, 4-chlorophenylalanine, 3,4-dichlorophenylalanine, 4-fluorophenylalanine, homoleucine, 4-methylphenylalanine, 1-naphthylalanine, 2-naphthylalanine, 4-nitrophenylalanine, 3-nitrotyrosine, 3-pyridylalanine, [2-thienyl]alanine.

Preferred non-polar side chain amino acids are glycine, valine, norvaline, leucine, isoleucine, norleucine, proline, phenylalanine, methionine and tryptophan.

Amino acids which have a polar side chain include serine, threonine, tyrosine, asparagines, glutamine, citrulline, homocitrulline, isoasparagine, β-homoglutamine, β-homoglutamine β-glutamine, β-homoserine, β-homothreonine, homoserine, isoserine.

Preferred such amino acids are serine, threonine, tyrosine, asparagines and glutamine.

Amino acids with a basic side chain include arginine, lysine, histidine, ornithine, diaminoacetic acid, diaminobutyric acid, and diaminopropionic acid. Preferred such amino acids include arginine and lysine. Arginine is particularly preferred.

Thus in a preferred embodiment, X1 is selected from glycine, valine, norvaline, leucine, isoleucine, norleucine, proline, phenylalanine, methionine and tryptophan, X2 is selected from serine, threonine, tyrosine, asparagines and glutamine and X3 is selected from arginine and lysine.

In a particular subclass of the above formula, the peptide may be a protegrin derivative of formula:

R-(Xa)-R-L-X1/2-Y-X2/3-Db-(R or a bond)-F-X1/2-X1/2-X2/3-X1/2-X1-R    (SEQ ID NO:4)

where Xa is either X1-X1 or a bond, or a fragment thereof of at least 7 amino acids.

Preferably where Xa is X1-X1, the two groups are the same.

More preferably, the formula is:

R-(Xa)-R-L-(G/S/A)-Y-(R/S)-Db-R-F-(G/S/A)-X1-(R/S)-(V/T)-G-R    (SEQ ID NO:5);

and most preferably the formula is:

R-(Xb)-R-L-(G/S/A)-Y-(R/S)-R-R-R-F-(G/S/A)-(T/I/V)-(R/S)-(V/T)-G-R    (SEQ ID NO:6)

where Xb is either a bond or A-A or G-G.

Examples of peptides of the above formula include:

R-G-G-R-L-S-Y-S-R-R-R-F-S-V-S-V-G-R (SEQ ID NO:7)

R-A-A-R-L-A-Y-R-L-L-R-F-A-I-R-V-G-R (SEQ ID NO:8)

R-A-A-R-L-G-Y-R-$_n$L-$_n$L-R-F-G-Z-R-V-G-R (SEQ ID NO:9)

R-G-G-R-L-S-Y-S-R-R-R-F-S-T-S-T-G-R (SEQ ID NO:10)

R-R-L-S-Y-S-R-R-R-F (SEQ ID NO:11)

in which $_n$L is norleucine, and Z is norvaline.

In another preferred embodiment, the peptide is a tachyplesin derivative of formula:

X1/X3-X1-X1/2-X1-R-X1-X1/2-X2-R-X1-X1-S/R-
X2-Db-X2/3-X2/3 (SEQ ID NO:12);

or a fragment thereof of at least 7 amino acids.

Preferably the two residues of Db are the same as each other.

Preferably this formula is:

(K/R/A)-W-(S/A)-F-R-X1-(S/A)-Y-R-X1-X1-(S/R)-
Y-Db'-(R/S)-(R/L/$_L$) (SEQ ID NO:13)

where Db' is selected from L-L, $_n$L-$_n$L and R-R (where $_n$L is norleucine).

More preferably, the formula is:

(R/K/A)-W-(S/A)-F-R-V-(S/A)-Y-R-G-I-(S/R)-Y-(R-
R-S/L-L-R)-(R/L) (SEQ ID NO:14).

Examples of peptides include:

K-W-S-F-R-V-S-Y-R-G-I-S-Y-R-R-S-R (SEQ ID NO:15);

R-W-S-F-R-V-S-Y-R-G-I-S-Y-R-R-S-R (SEQ ID NO:16);

K-W-A-F-R-V-A-Y-R-G-I-R-Y-L-L-R-L (SEQ ID NO:17); and

A-W-S-F-R-V-S-Y-R-G-I-S-Y-R-R-S-R (SEQ ID NO:18).

For the avoidance of doubt, in the above peptide formulae, the standard 1-letter amino acid code is used to represent the naturally occurring amino acids. Other letters are used as defined. The presence of alternative residues at one position is indicated as "/"; thus X1/2 means the residue in the peptide may be either of X1 or X2, and similarly R/S means that arginine or serine may occur where indicated.

All the peptides of the invention may comprise amino acids in the L-configuration or in the D-configuration. Further, these L- or D-peptides may be in the retroform, i.e. sequences in which the N- to C-terminal order is reversed. An example of such a peptide is:

R-S-R-R-Y-S-I-G-R-Y-S-V-R-F-S-W-A (SEQ ID NO:19), which is the retro form of the first tachyplesin-derived peptide shown in the preceding paragraph.

Fragments

Fragments of the above sequences which retain the ability of the peptide to cross a mammalian membrane may also be used. Generally, the fragments will be at least 7 amino acids in size. Preferably the peptides will be in the size range of 7 to 24 amino acids, such as 10 to 24, e.g. 10 to 20 in size. A typical size range within this is from 12 to 20 amino acids in size.

Basic Residues

Peptides and fragments of the invention contain a number of amino acids X3, which are preferably arginine or lysine.

It is preferred that peptides and fragments are selected to contain at least 4, preferably at least 5, and more preferably at least 6 residues X3.

N- and C-Terminal Extensions of the Peptides

Peptides (including fragments) of the invention will function as a vector for the enhancement of an immune response to an antigen. Where the antigen is attached to the N- or C-terminus of the peptide, the antigen may be attached directly by an amide bond, or indirectly via a linker. In the case of the latter, the linker may be from 1 to 25 amino acids and composed of any suitable peptide sequence. The linker may be a flexible linker of the type used to link antibody heavy and light chains together in a single chain antibody.

Where the N- or C-terminal of the peptide vector is not attached to the antigen, it may optionally contain a short amount of additional sequences, for example from 1 to 25 residues, which may for example be present for reasons conventional in the art of genetic engineering. For example, the sequence may form a short tag for purification or identification purposes, or may form a cleavable pre-sequence for transport out of a host cell in which the peptide-antigen fusion is produced.

Where the N-terminal of the peptide is not extended by the presence of additional sequences or is not linked to the antigen, the N-terminal of the peptide will generally comprise an amino group, though modifications to the group, such as those which may result from chemical synthesis of the peptide, may be present. Likewise, the C-terminal of a peptide may be a modified carboxy terminal, such as an amidated carboxy group or the like.

Retains the Ability to Cross a Mammalian Membrane.

By this term, it is meant that the peptide will be able to cross the cell membrane of a mammalian cell in culture at 37° C. to at least 50%, preferably at least 75% of the penetration achieved by the peptide SynB3 at a concentration of (both of) 1 µM, measured after 60 minutes in culture. The mammalian cell may be a primary cell line, a cancer cell line or any cell line generally available in the art, such as a K562 cells.

Antigen.

The antigen coupled to the peptide may be any antigen to which it is desired to provoke an immune response in a host mammal.

Antigens include peptides, whole proteins, and protein subunits.

The antigens may be viral, bacterial or derived from autologous proteins, for example for use in the treatment of autoimmune diseases or cancers.

Exemplary viral antigens include, but are not limited to, antigens derived from influenza virus; adenovirus; hepatitis A, B and C viruses; yellow fever virus; dengue fever virus; HIV-1 and HIV-2; HSV1 and HSV2; Epstein-Barr virus; Retroperitoneal fibromatosis associated herpes virus, Human papilloma virus, Kaposi's sarcoma herpes virus, and cytomegalovirus (CMV).

Exemplary bacterial antigens include, but are not limited to, antigens from infectious bacteria such as *Mycobacterium tuberculosis, Acne vulgaris, Propionibacterium acnes, Chlamydia trachomatis, Babesia microti, Ehrlichia risticii, Borrelia burgdorferi, Leishmania aethiopica, Candida albicans, Mycobacterium tuberculosis, Staphylococcus aureus, Staphylococcus pyogenes, Staphylococcus epidermis, Staphylococcus sapropyticus,* and *Trypanosoma cruzi.*

Self-antigens include antigens that appear on cells associated with the onset of autoimmune diseases or cancer.

Exemplary antigens are associated with the following cancers: Acute myelogenous leukaemia (AML), Acute lymphocytic leukaemia (ALL), Chronic myelogenous leukaemia (CML), Chronic lymphocytic leukemia (CLL), Hairy cell leukemia, Myeloma, and all solid tumors of all tissue types.

The accompanying examples illustrate the use of a peptide antigen of just 9 amino acids, and a 8.4 kDa protein derived from *M. tuberculosis*. Accordingly, the peptide vector may be used with a wide range of antigens, e.g. from a single peptide epitope of about 6 amino acids to proteins or subunits thereof of at least 200 kDa, though preferably no more than 100 Kda.

Antigens also include DNA or oligonucleotides that can be used for DNA-based vaccination where immunogenic proteins are expressed in in vivo transfected cells of the vaccine recipients in their native conformation from antigen-encoding expression plasmid DNA.

Mammal.

By "mammal", this is intended to be any mammal, including a human. Conjugates of the invention may be useful in veterinary medicine, e.g. for the vaccination of livestock and poultry or pets, as well as in human medicine.

Enhancing the Immune Response.

Conjugates of the invention will be useful in provoking an immune response in a subject mammal which is greater than the immune response which would be achieved in the mammal by the administration of an amount of unconjugated antigen equivalent to the amount of antigen in the conjugate. The ability of a conjugate to do this may be measured in a number of ways known in the art. An assay to measure CTL response in mice, illustrated in the accompanying examples, is one such method.

Preparation of Conjugates.

Conjugates may be prepared by chemical synthesis or by using molecular biology techniques. The antigen substance may be coupled to a peptide vector in the compositions according to the invention by any acceptable bonding means considering the chemical nature, the size and number of active and associated substances and peptides. They may be covalent, hydrophobic or ionic bonds, or cleavable or non-cleavable bounds in the physiological media or inside cells.

Coupling may be achieved in any site in the peptide vector in which functional groups such as —OH, —SH, —COOH, —$NH_2$ are naturally present or have been introduced. Thus an antigen molecule may be coupled to the peptide at the N-terminal or C-terminal ends, or in the peptide side chains.

Similarly, coupling may be achieved on any site in the antigen molecule, for example at which functional groups such as —OH, —SH, —COOH, —$NH_2$ are naturally present or have been introduced.

Coupling of the antigen may also occur by non-covalent means. For example, the vector peptide may comprise a group (e.g. streptavidin) which binds to a cognate group attached to the antigen (e.g. biotin). Ionic groups attached to the peptide vector and antigen may also provide suitable coupling. The linker may be designed to be cleavable within an APC, so as to facilitate the processing and presentation of the antigen. For example, a disulfide link may be used since these linkers are generally stable in plasma and reduced in the cell.

It is possible to couple more than one antigen to each vector peptide, and/or vice versa. This will depend to some extent on the relative sizes of the vector and antigen. Thus the ratio of peptide vector molecules to antigen molecules per conjugate may vary from 10:1 to 1:10, preferably from 5:1 to 1:5.

Where the peptide vector and antigen are joined by C- to N-terminal fusion (in either order), the fusion may be prepared as a single fusion protein by recombinant means.

Accordingly, another aspect of the invention is a nucleic acid molecule encoding such a fusion. The nucleic acid may be DNAs or RNAs and may be associated with control sequences such as a promoter and/or inserted in vectors. The vector used is chosen to be compatible with the host into which it will be transferred, to provide for expression of the fusion protein. Preparation of these vectors, and production or expression of peptides or compounds with a type (II) formula in a host, may be produced using molecular biology and genetic engineering techniques well known to those skilled in the art.

Thus in another embodiment, the invention provides a method of making a conjugate as defined above, which method comprises expressing in a host cell culture a nucleic acid sequence encoding said conjugate and recovering said conjugate from the culture.

Compositions.

Compositions of the invention comprise conjugates of the invention and a pharmaceutically acceptable carrier. Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s) in an amount effective to alleviate the symptoms of the subject being treated.

Dosage forms or compositions containing active ingredient in the range of 0.25 to 95% with the balance made up from non-toxic carrier may be prepared.

For oral administration, a pharmaceutically acceptable non-toxic composition is formed by the incorporation of any of the normally employed excipients, such as, for example, pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1%-95% active ingredient, more preferably 2-50%, most preferably 5-8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably, the composition will comprise 0.2-2% of the active agent in solution.

Doses and Routes of Administration.

The conjugate of the invention, for example in the form of a composition discussed above, may be administered by different pathways, for example by oral, rectal, nasal, topical (including buccal and sublingual), vaginal or parenteral (including subcutaneous, intramuscular, intravenous, intradermal, intrathecal and epidural) administration.

The effective amount of the conjugate of the invention to be administered will ultimately be at the discretion of the physician, taking into account the severity of the disease in a particular subject (e.g. a human patient or animal model) and the overall condition of the subject. Suitable doses will typically be in the range of 1 µg to 10 mg of antigen, more preferably between 10 µg and 1 mg of antigen, and still more preferably between 100 µg and 1 mg of antigen.

In order to induce an immune response in a mammalian subject, the conjugate may be administered in repeat doses, e.g. to provide booster doses at repeat intervals.

The conjugate may be used to boost the immunity of patients having a particular condition or to provide an immune response to a particular condition. Preferably, the conjugate provides a protective immune response to the condition.

Other advantages and characteristics of the invention will become clear after reading the following example concerning the preparation of compounds with a type (II) formula in which a peptide epitope and a protein antigens have been coupled to peptide vectors, and their enhancement of cell uptake and CTL response according to the invention.

EXAMPLES

Protocols

Peptide Synthesis

All peptides were synthesized according to Fmoc-tBu strategy using an AMS 422 (ABIMED, Germany). Labelling of the N-terminus of the peptides with NBD probe (4-fluoro-7-nitrobenzofurazan) was achieved as described elsewhere (Gazit et al., 1995 Biochemistry 34:11479-11488). Peptide purification was accomplished by reverse phase HPLC. Purification was over 95% for all peptides by the criterion of UV absorbance at 220 nm and 460 nm.

Coupling of SynB Vectors to the Recombinant Protein rDPV

The N-terminal amine of the rDPV protein was first derivatised with 2-Iminithiolane (2IT) in order to have a free thiol, while preserving the positive charge. Excess 2-IT reagent was removed from the protein by gel filtration. The 2IT-rDPV was then incubated with a thiopyridinium-activated 3MP-SynB peptide, to allow the formation of a disulfide bridge, by displacement of thiopyridinium from the 3MP-Peptide by the free thiol of 2IT-DPV. The displaced thiopyridinium was removed from the protein conjugate by gel-filtration. All the derivatisation steps were monitored using MALDI-TOF mass spectrometry.

Cell Uptake

Cell association was measured by flow cytometry using a FACScan (Becton Dickinson, USA). Free or vectorised compounds were incubated with K562 cells ($5\times10^5$ cells per ml) in Optimem medium at 37° C. for various periods of time.

Thereafter, the cells were washed twice and then resuspended in 0.5 ml of ice-cold PBS for FACS analysis. Cell-associated fluorophores were excited at 488 nm and fluorescence was measured at 525 nm. A histogram of fluorescence intensity per cell ($1\times10^4$) was obtained and the calculated mean of this distribution (Mean Fluorescence Intensity) was considered as representative of the amount of cell-associated peptide In Vivo Model Systems Mice (Balb/c) were immunized with either free or vectorised antigens, and mixed in with each formulation was 15 μg of Heparin. Reagents were mixed and then used to immunize subcutaneously in each flank. Mice were immunized on day 0 and after 3 weeks mice were sacrificed, spleens removed and single cell suspensions prepared. Three days later, stimulated Balb/c derived LPS blasts (using dextran sulphate and LPS) were irradiated and incubated with the antigen. Spleen cells ($6\times10^6$/ml) and LPS blast ($3\times10^6$/ml) were incubated together for 7 days. Cytotoxic T cell activity was measured on day 6 using $Cr^{51}$ labelled P815 cells either unpulsed or pulsed with the antigen as targets. On day 7, remaining cells are restimulated with antigen pulsed P815 cells with the addition of 20 U/ml of IL-2. All data has the non specific anti-P815 cells CTL subtracted.

Example 1

Delivery of a Peptide Epitope

| Compound | Sequence | Name |
|---|---|---|
| (I) | TYQRTRALV (SEQ ID NO:20) | Flu NP |
| (II) | AWSFRVSYRGISYRRSR-TYQRTRALV (SEQ ID NO:21) | SynB4/flu NP |
| (III) | RRLSYSRRRF-TYQRTRALV (SEQ ID NO:22) | SynB3/flu NP |

Cell Uptake

Flu NP epitope was conjugated to SynB3 and SynB4 vectors. First, we compared the cell uptake of free and conjugated flu NP. Flu NP epitope was conjugated to SynB3 and SynB4 vectors and labelled with a fluorescent group (NBD). The compounds were incubated with K562 cells for various times and the cell uptake was measured using flow cytometry.

Incubation of the cells with free flu NP epitope resulted in a very low uptake as judged by the mean of fluorescence intensity (FIG. 1). However, coupling the flu NP peptide antigen with either SynB3 or SynB4 vectors increased significantly its cell penetration. The cell penetration was very rapid in the first 30 min and then plateau thereafter. The enhancement of internalisation was 2- to 5-fold depending on the vector used. At 45 min, the cell uptake of SynB4/flu NP was about 5-fold higher than the one observed for free flu NP.

Immunization Studies

Balb/c mice (H-2d, female, 6-8 weeks) were immunized by the intradermal route (base of tail) with equimolar quantities of either free or conjugated flu NP peptide. Specifically, each mouse received 25 μg of flu NP peptide, either free, mixed with incomplete Freund's adjuvant (IFA), or conjugated. Conjugated peptide groups also received 15 μg of heparin. Spleens were harvested after three weeks. CTL responses were measured using the $^{51}$Cr release assay with splenocytes that had received two rounds of in vitro stimulation with free peptide.

Figure 2:
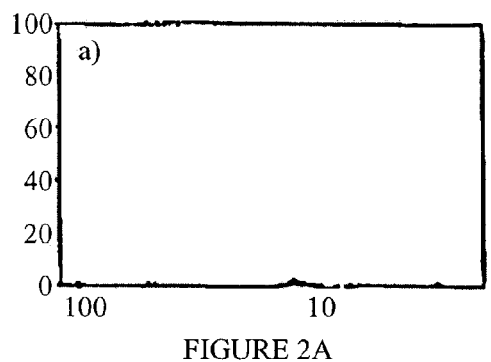
FIG. 2 shows the CTL responses elicited from mice immunized with controls ((a), (b) and (c)) and conjugates of the invention ((d) and (e)).
Figure 2:
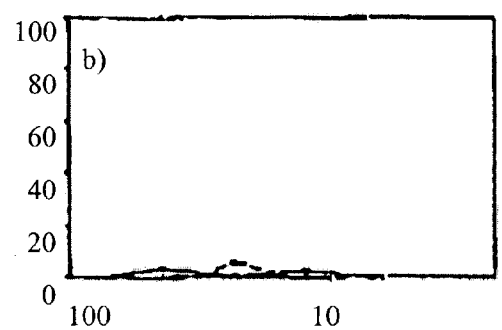
Figure 2:
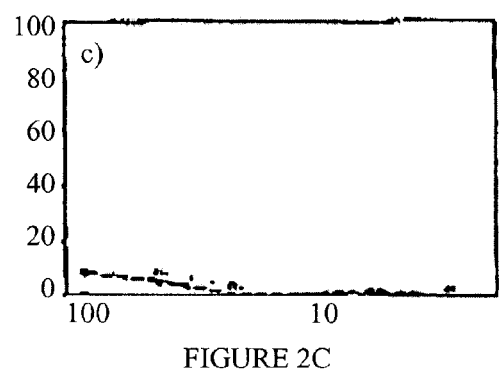
Figure 2:
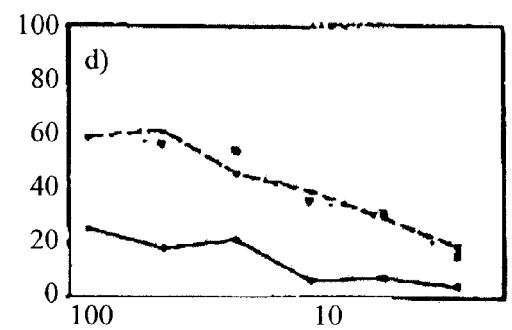
Figure 2:
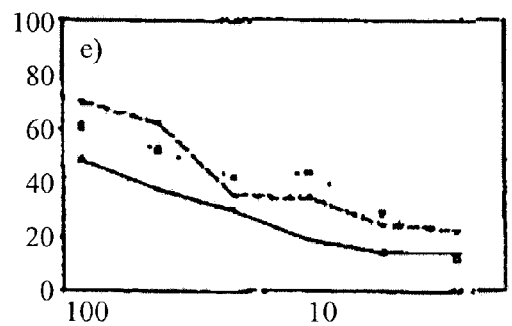

FIG. 2 shows the results of the flu NP experiment. Specifically, naive mice as well as mice that had received flu NP peptide alone failed to elicit specific CTL responses (a and b, respectively). Two of three mice that were immunized with flu NP peptide in IFA elicited weak CTL responses (c). In contrast, all mice that were immunized with either SynB3/flu NP (d) or SynB4/flu NP conjugates (e) elicited specific CTL responses, with five of the six mice eliciting strong CTL responses. FIG. 2 shows that the responses elicited by the flu NP peptide conjugates are clearly stronger than those elicited by free peptide or free peptide in IFA, a potent adjuvant.

Example 2

Delivery of a Recombinant Protein Antigen

| Compound | Sequence | Name |
|---|---|---|
| (IV) | RDPV | RDPV |
| (V) | AWSFRVSYRGISYRRSR-rDPV ((SEQ ID NO:18)-rDPV) | SynB4/rDPV |
| (VI) | RRLSYSRRRF-rDPV ((SEQ ID NO:11)-rDPV) | SynB3/rDPV |

Cell Uptake

We also coupled rDPV protein with SynB3 and SynB4 vectors. The coupling procedure is described in the Protocols. First, we compared the cell uptake of free and coupled rDPV. The rDPV was labelled with a fluorescent group (NBD) in order to measure its uptake. The compounds were incubated with K562 cells for various times and the cell uptake was measured using flow cytometry.

Figure 3:
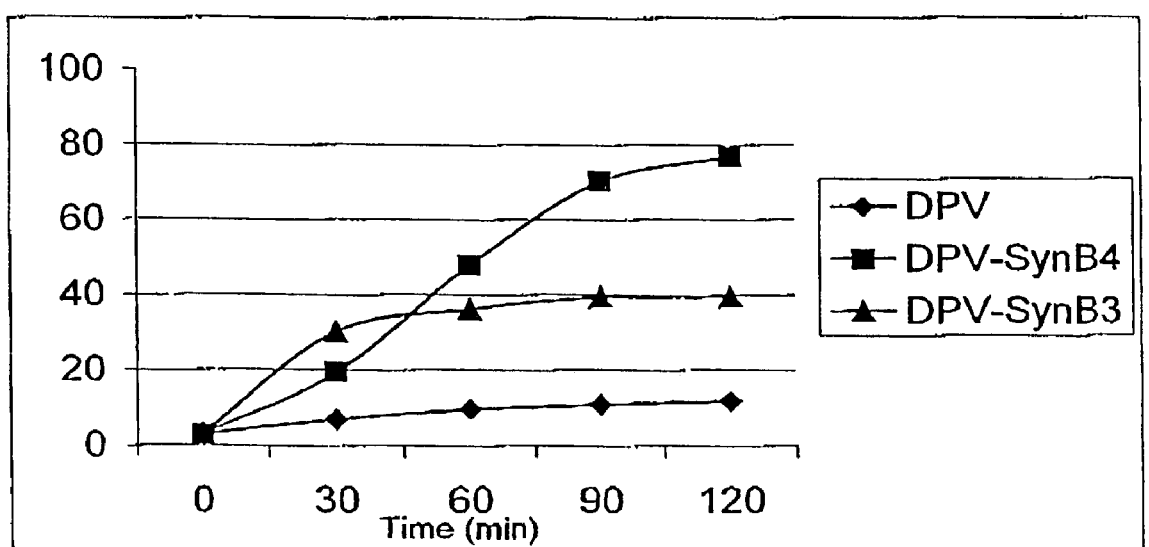
FIG. 3 shows the uptake of conjugates SynB3-DPV and SynB4-DPV by K562 cells, together with a control DPV protein. The x axis is time in minutes and the y axis denotes Mean Fluorescence Intensity.

Incubation of the cells with free rDPV resulted in a very low uptake as judged by the mean of fluorescence intensity (FIG. 3). However, coupling the rDPV protein with either SynB3 or SynB4 vectors increased significantly its cell penetration.

The enhancement of internalisation was 3- to 7-fold depending on the vector used. As observed for the peptide epitope, SynB4 vector enhanced rDPV cell penetration slightly better than SynB3. The cell uptake of rDPV-SynB3 reached saturation faster than the one with rDPV-SynB4 (30 min versus 100 min).

Immunization Studies

C57B1/6/c mice (female, 6-8 weeks) were immunized with 5 μg of either DPV protein, SynB3/rDPV conjugate, or SynB4/rDPV conjugate by the intradermal route (base of tail). The injection volume was 100 μl and also contained 15 μg of heparin. Animals were immunized on day 0 and day 21 with their spleens being harvested on day 42 for measurement of DPV specific CTL responses. CTL responses were measured using the $^{51}$Cr release assay with splenocytes that had received two rounds of in vitro stimulation.

Figure 4:
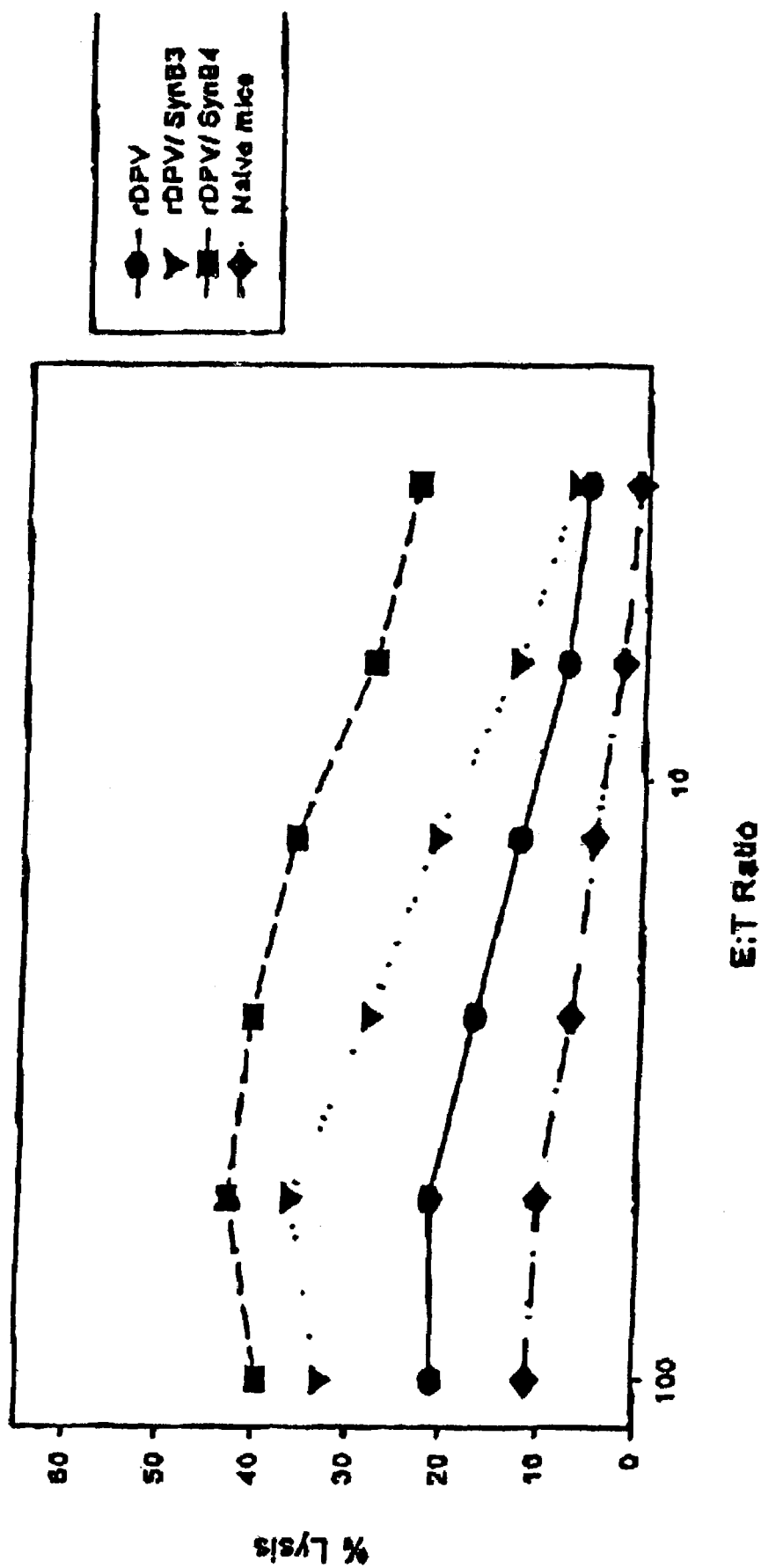
FIG. 4 shows CTL responses elicited from mice immunized with controls and DPV conjugates of the invention.

FIG. 4 shows the mean CTL responses for this rDPV experiment. Naive mice (diamonds) failed to elicit specific CTL response (where an effective response is defined as >10% specific lysis) while mice receiving rDPV protein alone elicited a weak CTL response (circles). In contrast, mice that were immunized with either the SynB3/rDPV or SynB4/rDPV conjugate elicited strong CTL responses (inverted-triangles and squares, respectively). FIG. 4 thus shows that the response elicited by the rDPV conjugates are clearly stronger than that elicited by free protein.

SEQUENCE LISTING

```
<160> NUMBER OF SEQ ID NOS: 22

<210> SEQ ID NO 1
<211> LENGTH: 13
<212> TYPE: PRT
<213> ORGANISM: Artificial Sequence
<220> FEATURE:
<221> NAME/KEY: SITE
```

```
<222> LOCATION: (1, 13)
<223> OTHER INFORMATION: Xaa may be either of an amino acid residue for
      which the side chain is non-polar, or an amino
      acid residue for which the side chain is basic
<220> FEATURE:
<221> NAME/KEY: SITE
<222> LOCATION: (2)
<223> OTHER INFORMATION: Xaa may be either of an amino acid residue for
      which the side chain is non-polar, or an amino
      acid residue for which the side chain is polar; or
      a bond
<220> FEATURE:
<221> NAME/KEY: SITE
<222> LOCATION: (3)
<223> OTHER INFORMATION: Xaa is any one of an amino acid residue for
      which the side chain is non-polar, or an amino acid residue for
      which the side chain is polar, or an amino acid residue for which
      the side chain is basic; or a bond
<220> FEATURE:
<221> NAME/KEY: SITE
<222> LOCATION: (4)
<223> OTHER INFORMATION: Xaa represents an amino acid residue for which
      the side chain is basic
<220> FEATURE:
<221> NAME/KEY: SITE
<222> LOCATION: (5)
<223> OTHER INFORMATION: Xaa represents an amino acid residue for which
      the side chain is non-polar; or a bond
<220> FEATURE:
<221> NAME/KEY: SITE
<222> LOCATION: (6)
<223> OTHER INFORMATION: Xaa represents an amino acid residue for which
      the side chain is non-polar
<220> FEATURE:
<221> NAME/KEY: SITE
<222> LOCATION: (7)
<223> OTHER INFORMATION: Xaa may be any one of an amino acid residue for
      which the side chain is non-polar, or an amino acid residue for
      which the side chain is polar, or an amino acid for which the side
      chain is basic
<220> FEATURE:
<221> NAME/KEY: SITE
<222> LOCATION: (8)
<223> OTHER INFORMATION: Xaa may be either of an amino acid residue for
      which the side chain is non-polar, or an amino
      acid residue for which the side chain is polar
<220> FEATURE:
<221> NAME/KEY: SITE
<222> LOCATION: (9, 12)
<223> OTHER INFORMATION: Xaa may be either of an amino acid residue for
      which the side chain is polar, or an amino acid
      residue for which the side chain is basic; or a
      bond
<220> FEATURE:
<221> NAME/KEY: SITE
<222> LOCATION: (10)..(11)
<223> OTHER INFORMATION: Xaa Xaa is either (X3-X3, in which each X3
      represents an amino acid residue for which the side chain is
      basic) or (X1-X1, in which each X1 represents an amino acid
      residue for which the side chain is non-polar)
<220> FEATURE:
<223> OTHER INFORMATION: Description of Artificial Sequence: Formula (I)

<400> SEQUENCE: 1

Xaa Xaa Xaa Xaa Xaa Xaa Xaa Xaa Xaa Xaa Xaa Xaa Xaa
1               5                   10

<210> SEQ ID NO 2
<211> LENGTH: 5
<212> TYPE: PRT
<213> ORGANISM: Artificial Sequence
<220> FEATURE:
<221> NAME/KEY: SITE
<222> LOCATION: (1)
<223> OTHER INFORMATION: Xaa may be either of an amino acid residue for
      which the side chain is non-polar, or an amino
      acid residue for which the side chain is basic
```

```
<220> FEATURE:
<221> NAME/KEY: SITE
<222> LOCATION: (2, 4)
<223> OTHER INFORMATION: Xaa represents an amino acid residue for which
      the side chain is non-polar
<220> FEATURE:
<221> NAME/KEY: SITE
<222> LOCATION: (3)
<223> OTHER INFORMATION: Xaa may be either of an amino acid residue for
      which the side chain is non-polar, or an amino
      acid residue for which the side chain is polar
<220> FEATURE:
<221> NAME/KEY: SITE
<222> LOCATION: (5)
<223> OTHER INFORMATION: Xaa represents an amino acid residue for which
      the side chain is basic
<220> FEATURE:
<223> OTHER INFORMATION: Description of Artificial Sequence: Nter of a
      linear derivative of a beta-stranded antibiotic peptide

<400> SEQUENCE: 2

Xaa Xaa Xaa Xaa Xaa
1               5

<210> SEQ ID NO 3
<211> LENGTH: 6
<212> TYPE: PRT
<213> ORGANISM: Artificial Sequence
<220> FEATURE:
<221> NAME/KEY: SITE
<222> LOCATION: (1, 2, 4)
<223> OTHER INFORMATION: Xaa may be either of an amino acid residue for
      which the side chain is non-polar, or an amino
      acid residue for which the side chain is polar
<220> FEATURE:
<221> NAME/KEY: SITE
<222> LOCATION: (3)
<223> OTHER INFORMATION: Xaa may be either of an amino acid residue for
      which the side chain is polar, or an amino acid
      residue for which the side chain is basic
<220> FEATURE:
<221> NAME/KEY: SITE
<222> LOCATION: (5)
<223> OTHER INFORMATION: Xaa represents an amino acid residue for which
      the side chain is non-polar
<220> FEATURE:
<221> NAME/KEY: SITE
<222> LOCATION: (6)
<223> OTHER INFORMATION: Xaa represents an amino acid residue for which
      the side chain is basic
<220> FEATURE:
<223> OTHER INFORMATION: Description of Artificial Sequence: Cter of a
      linear derivative of a beta-stranded antibiotic peptide

<400> SEQUENCE: 3

Xaa Xaa Xaa Xaa Xaa Xaa
1               5

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Linear
      derivative of a beta-stranded antibiotic peptide
<220> FEATURE:
<221> NAME/KEY: SITE
<222> LOCATION: (2..3)
<223> OTHER INFORMATION: Xaa Xaa is either X1-X1, in which each X1,
      which may be identical or different, represents an amino acid
      residue for which the side chain is non-polar, or a bond
<220> FEATURE:
<221> NAME/KEY: SITE
<222> LOCATION: (6, 13, 14, 16)
<223> OTHER INFORMATION: Xaa may be either of an amino acid residue for
```

```
        which the side chain is non-polar, or an amino
        acid residue for which the side chain is polar
<220> FEATURE:
<221> NAME/KEY: SITE
<222> LOCATION: (8, 15)
<223> OTHER INFORMATION: Xaa may be either of an amino acid residue for
        which the side chain is polar, or an amino acid
        residue for which the side chain is basic
<220> FEATURE:
<221> NAME/KEY: SITE
<222> LOCATION: (9..10)
<223> OTHER INFORMATION: Xaa Xaa is either (X3-X3, in which each X3
        represents an amino acid residue for which the side chain is
        basic) or (X1-X1, in which each X1 represents an amino acid
        residue for which the side chain is non-polar)
<220> FEATURE:
<221> NAME/KEY: SITE
<222> LOCATION: (11)
<223> OTHER INFORMATION: Xaa is Arg or a bond
<220> FEATURE:
<221> NAME/KEY: SITE
<222> LOCATION: (17)
<223> OTHER INFORMATION: Xaa represents an amino acid residue for which
        the side chain is non-polar

<400> SEQUENCE: 4

Arg Xaa Xaa Arg Leu Xaa Tyr Xaa Xaa Xaa Xaa Phe Xaa Xaa Xaa Xaa
1               5                   10                  15

Xaa Arg

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Linear
        derivative of a beta-stranded antibiotic peptide
<220> FEATURE:
<221> NAME/KEY: SITE
<222> LOCATION: (2..3)
<223> OTHER INFORMATION: Xaa Xaa is either X1-X1, in which each X1,
        which may be identical or different, represents an amino acid
        residue for which the side chain is non-polar, or a bond
<220> FEATURE:
<221> NAME/KEY: SITE
<222> LOCATION: (6, 13)
<223> OTHER INFORMATION: Xaa is Gly or Ser or Ala
<220> FEATURE:
<221> NAME/KEY: SITE
<222> LOCATION: (8, 15)
<223> OTHER INFORMATION: Xaa is Arg or Ser
<220> FEATURE:
<221> NAME/KEY: SITE
<222> LOCATION: (9..10)
<223> OTHER INFORMATION: Xaa Xaa is either (X3-X3, in which each X3
        represents an amino acid residue for which the side chain is
        basic) or (X1-X1, in which each X1 represents an amino acid
        residue for which the side chain is non-polar)
<220> FEATURE:
<221> NAME/KEY: SITE
<222> LOCATION: (14)
<223> OTHER INFORMATION: Xaa represents an amino acid residue for which
        the side chain is non-polar
<220> FEATURE:
<221> NAME/KEY: SITE
<222> LOCATION: (16)
<223> OTHER INFORMATION: Xaa is Val or Thr

<400> SEQUENCE: 5

Arg Xaa Xaa Arg Leu Xaa Tyr Xaa Xaa Xaa Arg Phe Xaa Xaa Xaa Xaa
1               5                   10                  15

Gly Arg
```

```
<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Linear
      derivative of a beta-stranded antibiotic peptide
<220> FEATURE:
<221> NAME/KEY: SITE
<222> LOCATION: (2..3)
<223> OTHER INFORMATION: Xaa-Xaa is either a bond or Ala-Ala or Gly-Gly
<220> FEATURE:
<221> NAME/KEY: SITE
<222> LOCATION: (6, 13)
<223> OTHER INFORMATION: Xaa is Gly or Ser or Ala
<220> FEATURE:
<221> NAME/KEY: SITE
<222> LOCATION: (8, 15)
<223> OTHER INFORMATION: Xaa is Arg or Ser
<220> FEATURE:
<221> NAME/KEY: SITE
<222> LOCATION: (14)
<223> OTHER INFORMATION: Xaa is Thr or Ile or Val
<220> FEATURE:
<221> NAME/KEY: SITE
<222> LOCATION: (16)
<223> OTHER INFORMATION: Xaa is Val or Thr

<400> SEQUENCE: 6

Arg Xaa Xaa Arg Leu Xaa Tyr Xaa Arg Arg Arg Phe Xaa Xaa Xaa Xaa
1               5                   10                  15

Gly Arg

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Linear
      derivative of a beta-stranded antibiotic peptide

<400> SEQUENCE: 7

Arg Gly Gly Arg Leu Ser Tyr Ser Arg Arg Arg Phe Ser Val Ser Val
1               5                   10                  15

Gly Arg

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Linear
      derivative of a beta-stranded antibiotic peptide

<400> SEQUENCE: 8

Arg Ala Ala Arg Leu Ala Tyr Arg Leu Leu Arg Phe Ala Ile Arg Val
1               5                   10                  15

Gly Arg

<210> SEQ ID NO 9
<211> LENGTH: 18
<212> TYPE: PRT
<213> ORGANISM: Artificial Sequence
<220> FEATURE:
<221> NAME/KEY: MOD_RES
<222> LOCATION: (9, 10)
<223> OTHER INFORMATION: Nle
<220> FEATURE:
<221> NAME/KEY: MOD_RES
<222> LOCATION: (14)
```

```
<223> OTHER INFORMATION: Nva
<220> FEATURE:
<223> OTHER INFORMATION: Description of Artificial Sequence: Linear
      derivative of a beta-stranded antibiotic peptide

<400> SEQUENCE: 9

Arg Ala Ala Arg Leu Gly Tyr Arg Xaa Xaa Arg Phe Gly Xaa Arg Val
1               5                   10                  15

Gly Arg

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Linear
      derivative of a beta-stranded antibiotic peptide

<400> SEQUENCE: 10

Arg Gly Gly Arg Leu Ser Tyr Ser Arg Arg Phe Ser Thr Ser Thr
1               5                   10                  15

Gly Arg

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Linear
      derivative of a beta-stranded antibiotic peptide

<400> SEQUENCE: 11

Arg Arg Leu Ser Tyr Ser Arg Arg Arg Phe
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Linear
      derivative of a beta-stranded antibiotic peptide
<220> FEATURE:
<221> NAME/KEY: SITE
<222> LOCATION: (12)
<223> OTHER INFORMATION: Xaa is Ser or Arg
<220> FEATURE:
<221> NAME/KEY: SITE
<222> LOCATION: (1)
<223> OTHER INFORMATION: Xaa may be either of an amino acid residue for
      which the side chain is non-polar, or an amino acid
      residue for which the side chain is basic
<220> FEATURE:
<221> NAME/KEY: SITE
<222> LOCATION: (2, 4, 6, 10, 11)
<223> OTHER INFORMATION: Xaa represents an amino acid residue for which
      the side chain is non-polar
<220> FEATURE:
<221> NAME/KEY: SITE
<222> LOCATION: (3, 7)
<223> OTHER INFORMATION: Xaa may be either of an amino acid residue for
      which the side chain is non-polar, or an amino
      acid residue for which the side chain is polar
<220> FEATURE:
<221> NAME/KEY: SITE
<222> LOCATION: (8, 13)
<223> OTHER INFORMATION: Xaa represents an amino acid residue for which
      the side chain is polar
<220> FEATURE:
<221> NAME/KEY: SITE
<222> LOCATION: (14..15)
```

```
<223> OTHER INFORMATION: Xaa Xaa is either (X3-X3, in which each X3
      represents an amino acid residue for which the side chain is
      basic) or (X1-X1, in which each X1 represents an amino acid
      residue for which the side chain is non-polar)
<220> FEATURE:
<221> NAME/KEY: SITE
<222> LOCATION: (16, 17)
<223> OTHER INFORMATION: Xaa may be either of an amino acid residue for
      which the side chain is polar, or an amino acid
      residue for which the side chain is basic

<400> SEQUENCE: 12

Xaa Xaa Xaa Xaa Arg Xaa Xaa Xaa Arg Xaa Xaa Xaa Xaa Xaa Xaa Xaa
1               5                   10                  15

Xaa

<210> SEQ ID NO 13
<211> LENGTH: 17
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Lys or Arg or Ala
<220> FEATURE:
<221> NAME/KEY: SITE
<222> LOCATION: (3, 7)
<223> OTHER INFORMATION: Xaa is Ser or Ala
<220> FEATURE:
<221> NAME/KEY: SITE
<222> LOCATION: (6, 10, 11)
<223> OTHER INFORMATION: Xaa represents an amino acid residue for which
      the side chain is non-polar
<220> FEATURE:
<221> NAME/KEY: SITE
<222> LOCATION: (12, 16)
<223> OTHER INFORMATION: Xaa is Ser or Arg
<220> FEATURE:
<221> NAME/KEY: SITE
<222> LOCATION: (14..15)
<223> OTHER INFORMATION: Xaa-Xaa is selected from Leu-Leu, Nle-Nle and
      Arg-Arg
<220> FEATURE:
<221> NAME/KEY: SITE
<222> LOCATION: (17)
<223> OTHER INFORMATION: Xaa is Arg or Leu or Nle
<220> FEATURE:
<223> OTHER INFORMATION: Description of Artificial Sequence: Linear
      derivative of a beta-stranded antibiotic peptide

<400> SEQUENCE: 13

Xaa Trp Xaa Phe Arg Xaa Xaa Tyr Arg Xaa Xaa Xaa Tyr Xaa Xaa Xaa
1               5                   10                  15

Xaa

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Linear
      derivative of a beta-stranded antibiotic peptide
<220> FEATURE:
<221> NAME/KEY: SITE
<222> LOCATION: (1)
<223> OTHER INFORMATION: Xaa is Lys or Arg or Ala
<220> FEATURE:
<221> NAME/KEY: SITE
<222> LOCATION: (3, 7)
<223> OTHER INFORMATION: Xaa is Ser or Ala
<220> FEATURE:
<221> NAME/KEY: SITE
<222> LOCATION: (12)
```

```
<223> OTHER INFORMATION: Xaa is Ser or Arg
<220> FEATURE:
<221> NAME/KEY: SITE
<222> LOCATION: (17)
<223> OTHER INFORMATION: Xaa is Arg or Leu

<400> SEQUENCE: 14

Xaa Trp Xaa Phe Arg Val Xaa Tyr Arg Gly Ile Xaa Tyr Arg Arg Arg
1               5                   10                  15

Xaa

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Linear
      derivative of a beta-stranded antibiotic peptide

<400> SEQUENCE: 15

Lys Trp Ser Phe Arg Val Ser Tyr Arg Gly Ile Ser Tyr Arg Arg Ser
1               5                   10                  15

Arg

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Linear
      derivative of a beta-stranded antibiotic peptide

<400> SEQUENCE: 16

Arg Trp Ser Phe Arg Val Ser Tyr Arg Gly Ile Ser Tyr Arg Arg Ser
1               5                   10                  15

Arg

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Linear
      derivative of a beta-stranded antibiotic peptide

<400> SEQUENCE: 17

Lys Trp Ala Phe Arg Val Ala Tyr Arg Gly Ile Arg Tyr Leu Leu Arg
1               5                   10                  15

Leu

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Linear
      derivative of a beta-stranded antibiotic peptide

<400> SEQUENCE: 18

Ala Trp Ser Phe Arg Val Ser Tyr Arg Gly Ile Ser Tyr Arg Arg Ser
1               5                   10                  15

Arg

<210> SEQ ID NO 19
```

```
<211> LENGTH: 17
<212> TYPE: PRT
<213> ORGANISM: Artificial Sequence
<220> FEATURE:
<223> OTHER INFORMATION: Description of Artificial Sequence: Linear
      derivative of a beta-stranded antibiotic peptide

<400> SEQUENCE: 19

Arg Ser Arg Arg Tyr Ser Ile Gly Arg Tyr Ser Val Arg Phe Ser Trp
1               5                   10                  15

Ala

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Flu NP

<400> SEQUENCE: 20

Thr Tyr Gln Arg Thr Arg Ala Leu Val
1               5

<210> SEQ ID NO 21
<211> LENGTH: 26
<212> TYPE: PRT
<213> ORGANISM: Artificial Sequence
<220> FEATURE:
<223> OTHER INFORMATION: Description of Artificial Sequence: SynB4/flu
      NP

<400> SEQUENCE: 21

Ala Trp Ser Phe Arg Val Ser Tyr Arg Gly Ile Ser Tyr Arg Arg Ser
1               5                   10                  15

Arg Thr Tyr Gln Arg Thr Arg Ala Leu Val
            20                  25

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: SynB3/flu
      NP

<400> SEQUENCE: 22

Arg Arg Leu Ser Tyr Ser Arg Arg Phe Thr Tyr Gln Arg Thr Arg
1               5                   10                  15

Ala Leu Val
```

The invention claimed is:

1. A cytotoxic T lymphocyte (CTL)-inducing conjugate of an antigen coupled to a tachyplesin peptide lacking one or more disulfide bonds, wherein said peptide is of the formula:

A-W-S-F-R-V-S-Y-R-G-I-S-Y-R-R-S-R    (SEQ ID NO:18).

2. The CTL-inducing conjugate according to claim 1 wherein said antigen is selected from the group consisting of a peptide, a whole protein, and a protein subunit.

3. The CTL-inducing conjugate according to claim 2 wherein the source of said peptide, protein or protein subunit antigen is selected from the group consisting of a virus, a bacteria, a mammalian protein and a cancer protein.

4. The CTL-inducing conjugate according to claim 3, wherein said virus is an influenza virus.

5. A composition comprising the CTL-inducing conjugate of claim 1 in a pharmaceutically acceptable carrier.

6. A method of enhancing the immune response of a mammal to an antigen which comprises administering to the mammal the CTL-inducing conjugate of claim 1.

7. A method of preparing the CTL-inducing conjugate of claim 1 comprising the steps of:
  (a) expressing in a host cell a nucleic acid encoding said CTL-inducing conjugate, wherein said peptide is fused to said antigen, and
  (b) recovering said CTL-inducing conjugate from said host cell.

* * * * *